(12) United States Patent
Sardari et al.

(10) Patent No.: US 8,569,361 B1
(45) Date of Patent: Oct. 29, 2013

(54) ALIPHATIC AMINO ACID BIOSYNTHESIS INHIBITORS AND A METHOD OF SYNTHESIZING THE SAME

(76) Inventors: Soroush Sardari, Tehran (IR); Vahid Khalaj, Tehran (IR); Mahdieh Mahboobi Khomeini, Tehran (IR); Parisa Azerang, Tehran (IR)

(*) Notice: Subject to any disclaimer, the term of this patent is extended or adjusted under 35 U.S.C. 154(b) by 0 days.

(21) Appl. No.: 13/525,319

(22) Filed: Jun. 17, 2012

Related U.S. Application Data

(60) Provisional application No. 61/639,890, filed on Apr. 28, 2012.

(51) Int. Cl.
*A61K 31/352* (2006.01)
*C07D 311/16* (2006.01)

(52) U.S. Cl.
USPC .......................................... 514/457; 549/399

(58) Field of Classification Search
USPC .......................................... 549/399; 514/457
See application file for complete search history.

(56) References Cited

PUBLICATIONS

Ramachandran et al., Stereoselective sythesis of hex-2-(E)-en-4-yl-1,6-dioates and E,Z-muconic acid diesters via organo-catalyzed self-coupling of propiolates, 2005, Tetrahedron Letters, 46, 2547-2549.*

* cited by examiner

*Primary Examiner* — Kristin Bianchi
(74) *Attorney, Agent, or Firm* — Barry Choobin; Patent360 LLC

(57) ABSTRACT

The embodiments herein provide a composition and a method of synthesizing a composition comprising an aliphatic amino acid biosynthesis inhibitor having an antifungal activity. The composition comprises 2-oxo-2H-chromen-7-yl propiolate, diethyl-hex-2-en-4-yne-dioate and dinonyl-hex-2-en-4-yne-dioate. The composition inhibits a biosynthesis of an aliphatic amino acid in a fungal biological system. The aliphatic amino acid is selected from a group consisting of leucine, isoleucine and valine. The composition is used with a concentration of 0-200 μg/ml. The method comprises mixing solutions of dicyclohexylcarbodiimide (DCC) and Dimethylaminopyridine (DMAP) with alcohol, acetylene carboxylic acid and dichloromethane to obtain a mixture which is stirred filtered and washed with ether. The solvents are evaporated to obtain a residue that is dissolved in dichloromethane and stirred with a catalyst. The extra solvents are evaporated to obtain the derivative compound and purified by silica gel column chromatography.

12 Claims, 9 Drawing Sheets

ALIPHATIC AMINO ACID BIOSYNTHESIS INHIBITORS AND A METHOD OF SYNTHESIZING THE SAME

CROSS-REFERENCE TO RELATED APPLICATION

This application claims the priority under 35 USC 119(e) of U.S. Provisional Application Ser. No. 61/639,890, filed Apr. 28, 2012, which included by reference herein.

SPONSORSHIP STATEMENT

The present invention is sponsored by PASTEUR INSTITUTE OF IRAN.

BACKGROUND

1. Technical Field

The embodiments herein generally relate antibiotics used for a treatment of infectious diseases. The embodiments herein particularly relate to antifungal compounds used for a treatment of infectious diseases such systemic infections in immuno-compromised patients. The embodiments herein more particularly relate to antifungal agents with new mechanism of actions for treating patients with life threatening systemic fungal disease. The embodiments herein also relate to derivatives with an anti-fungal activity, which are capable of inhibiting a biosynthesis of aliphatic amino acid in fungal biological systems. The embodiments herein further relate to a method of synthesizing the newly developed derivatives having an anti-fungal activity. such as aliphatic amino acid biosynthesis inhibitors and a method for determining a mode of action of antifungal compound using reversal assay and molecular techniques 2. Description of the Related Art Antibiotics are chemical substances with inhibitory or lethal activity on certain organisms. The chemical compositions and the mode of action of antibiotics are diverse. The antibiotics generally exert their inhibitory effects by preventing the cell wall biosynthesis, by inhibiting the protein synthesis, by blocking nucleic acid biosynthesis and through various other unknown mechanisms.

The antibiotics are the essential elements for a successful treatment of any infectious disease. Inspite of their availability, there are still several reasons for exploring the new drugs inevitable. The emergence of drug resistant lethal pathogens has become a significant reason towards the discovery of new drugs. Moreover the significant side-effects of certain drugs coupled with a poor treatment outcome have led to the search for more efficacious and less toxic drugs.

In the recent years, the fungal pathogens have become a major cause of infection in humans with a high mortality rate such as systemic infections in the immuno-compromised patients. A very few number of antifungal drugs are available. However resistant isolates have also been identified. Still there is a need for the antifungal agents with new mechanisms of action for treating the increasing number of patients suffering from the life-threatening systemic fungal diseases. There is also a need to overcome the increasing problems of resistance happening with the current therapies.

The increasing number of fungal resistant against drugs put an emphasis on the significance for searching the new antifungal drugs. Although a screening of natural and chemical sources is one of the main ways for finding the new antifungal combinations. The pharmacology of the combination is important for the pharmaceutical industries. One of the methods for recognizing a reaction mechanism is a reversal assay method. The reversal assay method is performed based on the metabolic mediation capability of a final product of blocked route by the intended drug in deactivating the drug.

About 400 million dollars are annually allocated to an import of the pharmaceutical raw materials to a country. In the last few years, the Scrip journal announced that the maximum rate of sales in two of the greatest pharmaceutical products in Iran is related to antibiotics (24 percent valued at 9.6 million dollar). The antibiotics are the chemical substances which are either taken from the microorganisms like fungi and bacteria or made synthetically. The antibiotics prevent the eukaryotic or prokaryotic cells from living or hinder their proliferation. The components of antibiotics are different depending on the work done by them.

The usage of anti-microbial agents is necessary for a successful treatment of the infectious diseases. Although there are many pharmaceutical categories which are used for treating the infectious diseases in the human beings. The design of the drug and the production of new anti-microbial agents is significant due to several reasons. During the last decade, the resistance in the microorganisms which are considered to be the common pathogens in human beings has been increased. This increase in the resistance has restricted the options of antimicrobial agents which can be used for a treatment of the exclusive organisms. The new antimicrobial agents are also required for a determined group of the microorganisms. A limited number of antimicrobial agents are available for a treatment of the infections caused by fungi. The infections caused by these organisms has created serious concerns.

The fungal pathogens can be divided into two groups called real fungi and opportunistic fungi. The first group is able to harm the human beings naturally. But the second group is mostly seen in those who suffer from immunosuppression, for example, human beings suffering from the diseases such as AIDS, cancer, and organ donation. The fungal infections may be systemic or topical. The systemic infections involve many parts of the body so that they are more significant. Many fungus existing in the nature are superficially harmless. However most of the fungal diseases in the human beings are related to the fungus.

During the last thousand years, many infectious diseases have been discovered and during the last 30 years various new diseases have been discovered. The microorganisms are continuosly changing and finding new places for living and new ways for becoming compatible with the situation. The harmless microorganisms may turn to fatal types and the fatal microorganisms may get transferred from their normal host to the human beings. As the discovery of new infectious diseases continues and new ways and processes of disease by the pathogen agents are created, a production of new antimicrobial agents which are capable of being used for the treatment of these infections seems to be significant. A creation of new pharmaceutical categories with less side effects and shorter therapeutic time for fighting against infectious diseases is of high significance.

Although there are a large number of antibiotics available in the market today but the availability of antifungal antibiotics is very less. However this group of drugs plays an outstanding role in controlling the fungal diseases. Still there are a limited number of antifungal agents currently available for treating the threatening fungal infections.

Although there have been more options for the antifungal drugs against the fungal infections in the last thirty years, the pharmacologic principles of an antifungal treatment are not thoroughly recognized. An estimation of a therapeutic concentration of the antifungal drugs would be difficult without achieving any reasonable results from a concentration of a drug required for ceasing a growth of fungus in a laboratory environment.

Although the screening of various chemical or natural libraries has been a useful approach for a discovery of the new antifungal compounds their mode of action is important for the pharmaceutical industries. There are new pharmaceutical molecules that do not enjoy any ideal feature but they are capable of achieving the desirable stages and they can be optimized during a drug development process. The mode of action (MOA) of many of the antimicrobial drugs is totally unrecognized since an elucidation mechanism of many of them is difficult and undetectable. In many cases, a complicated mechanism is applied for the antibiotics for an instant and an intensive effect on an intended cell.

Hence there is a need to develop a method for determining a mechanism of action of the anti-fungal drugs. Also there is a need to utilize these methods for developing the anti-resistant drugs where the determined mechanism of action of the anti-fungal drugs is used to overcome a resistance caused to the antifungal drugs by the fungus. Further there is a need to develop the anti-fungal agents or combinations that work by inhibiting a synthesis of the aliphatic amino acids in the fungus thereby inhibiting their growth.

The above mentioned shortcomings, disadvantages and problems are addressed herein and which will be understood by reading and studying the following specification.

OBJECTIVES OF THE EMBODIMENTS

The primary objective of the embodiments herein is to develop hex-2-en-4-yne-diote derivatives with antifungal activity.

Another objective of the embodiments herein is to develop hex-2-en-4-yne-diote derivatives with anti-fungal activities for treating patients with life threatening systemic fungal diseases.

Yet another objective of the embodiments herein is to develop hex-2-en-4-yne-diote derivatives with a capability to inhibit a biosynthesis of an aliphatic amino acid in the fungal biological systems.

Yet another objective of the embodiments herein is to develop newly anti-fungal compounds having their structure different from the existing anti-fungal drugs.

Yet another objective of the embodiments herein is to develop the anti-fungal compounds that are synthesized on a large scale.

Yet another objective of the embodiments herein is to develop the new bioactive compounds that are used as a standard for the biochemical studies.

Yet another objective of the embodiments herein is to develop the new compounds that are used as patterns in a design development process of the other new drugs.

Yet another objective of the embodiments herein is to develop the anti-fungal compounds that are used in agriculture.

Yet another objective of the embodiments herein is to develop the compounds that are used in a textile industry.

Yet another objective of the embodiments herein is to develop the compounds that are used in the textile industry for the production of the anti-fungal fabrics.

Yet another objective of the embodiments herein is to develop the compounds that inhibit a growth of the fungi which are resistant to current anti-fungal drugs.

Yet another objective of the embodiments herein is to develop the compounds that have a property of inhibiting the target enzymes.

Yet another objective of the embodiments herein is to develop the compounds that are utilized for studying the crystallization studies of other compounds.

Yet another objective of the embodiments herein is to develop a method for determining a mechanism of action of the anti-fungal drugs.

Yet another objective of the embodiments herein is to develop a method for determining a mechanism of action of anti-fungal drugs using a reversal assay technique.

Yet another objective of the embodiments herein is to provide a method for developing the anti-resistant drugs and to provide a method to overcome a resistance caused by the fungi to the antifungal drugs by using the determined mechanism of action of the anti-fungal drugs.

Yet another objective of the embodiments herein to develop a method for synthesizing a wide range of similar compounds.

These and other objects and advantages of the embodiments herein will become readily apparent from the following detailed description taken in conjunction with the accompanying drawings.

SUMMARY

The various embodiments herein provide new chemical compounds and a method of synthesizing the new chemical compounds. The new chemical compounds have anti-fungal activities. The new chemical compounds inhibit the biosynthesis of aliphatic amino acid in the fungal systems. The aliphatic amino acids are essential for the growth of fungi.

The embodiments herein provide a composition and a method of synthesizing a composition comprising an aliphatic amino acid biosynthesis inhibitor having an antifungal activity. According to one embodiment herein, an aliphatic amino acid biosynthesis inhibitor composition having an antifungal activity comprises a compound A, a compound B, a compound C and a compound D.

The compound A is 2-oxo-2H-chromen-7-yl propiolate and the compound 2-oxo-2H-chromen-7-yl propiolate is shown by formula (1)

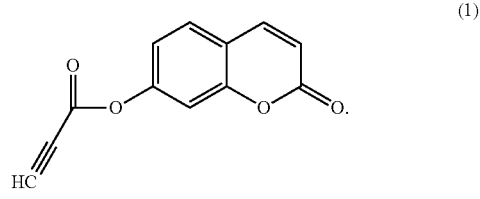 [SMILES: C#CC(=O)Oc1ccc2ccc(=O)oc2c1]

(1)

The compound B is diethyl-hex-2-en-4-yne-dioate and the compound diethyl-hex-2-en-4-yne-dioate is shown by formula (2)

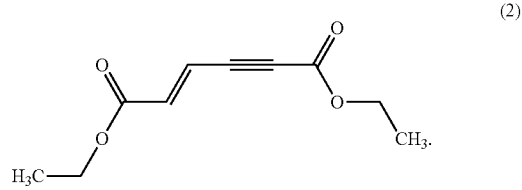

(2)

The compound C is dinonyl-hex-2-en-4-yne-dioate and the compound dinonyl-hex-2-en-4-yne-dioate is shown by formula (3)

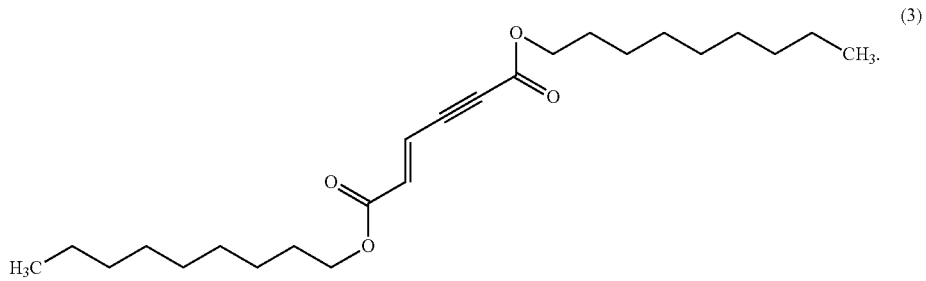 [SMILES: CCCCCCCCCOC(=O)C#C/C=C/C(=O)OCCCCCCCCC]

(3)

The compound D is shown by formula (4)

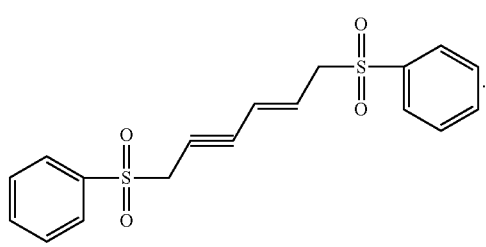

(4)

According to an embodiment herein, the composition inhibits a biosynthesis of an aliphatic amino acid in a fungal biological system. The aliphatic amino acid is selected from a group consisting of leucine, isoleucine and valine. The composition is used with a concentration of 0-200 μg/ml.

According to an embodiment herein, a method of synthesizing an aliphatic amino acid biosynthesis inhibitor composition having an antifungal activity. The method comprises preparing a solution A and a solution B. The solution A is prepared by mixing a compound E and a compound F. The solution B is prepared by mixing a compound containing a hydroxyl group, an acetylene carboxylic acid and a solvent.

The prepared solution A is added to a prepared solution B at a predetermined temperature range drop wise over a predetermined time period to obtain a first mixture. The predetermined temperature range is 0° C.-4° C. and the predetermined time period is 1 hr.

Further, the first mixture is stirred for a predetermined time to obtain a residue. The predetermined time is 5 hrs. The residue is dissolved in the solvent at a predefined temperature to obtain a second mixture. The solvent is dichloromethane. The predefined temperature is 0° C. The second mixture is stirred with a catalyst for a predefined time. The predefined time is 30 minutes. The stirred second mixture is evaporated to obtain a compound. The compound is hex-2-en-4-yn-1,6-dioate derivative compound.

The compound E is dicyclohexylcarbodiimide (DCC) and the compound F is Dimethylaminopyridine (DMAP). The compound containing the hydroxyl group includes 7-hydroxy-chromen-2-one, ethanol and nonane-1-ol. The acetylene carboxylic acid is propiolic acid. The solvent is dichloromethane.

The residue includes 2-oxo-2H-chromen-7-yl propiolate, ethyl propiolate, dodecyl propiolate and (Ethynylsulfonyl) benzene.

The catalysts include N,N'-Dicyclohexylcarbodiimide (DCC), 4-Dimethylaminopyridine (DMAP), and 1,4-diazabicyclo[2.2.2]octane (DABCO).

The composition includes a compound A, a compound B, a compound C and a compound D. The compound A is 2-oxo-2H-chromen-7-yl propiolate and The compound 2-oxo-2H-chromen-7-yl propiolate is shown by formula (1)

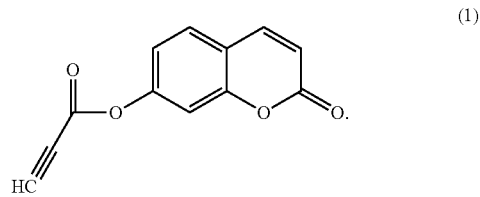

(1)

The compound B is diethyl-hex-2-en-4-yne-dioate and the compound diethyl-hex-2-en-4-yne-dioate is shown by formula (2)

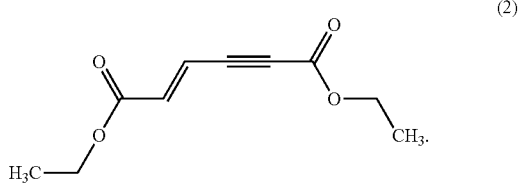

(2)

The compound C is dinonyl-hex-2-en-4-yne-dioate and the compound dinonyl-hex-2-en-4-yne-dioate is shown by formula (3)

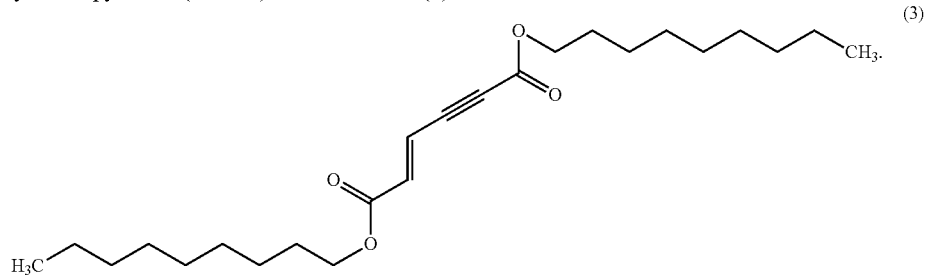

(3)

The compound D is shown by formula (4)

$$\text{(4)}$$

The composition inhibits a biosynthesis of an aliphatic amino acid in a fungal biological system. The amino acid is selected from a group consisting of leucine, isoleucine and valine. The composition is used with a concentration of 0-200 µg/ml.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
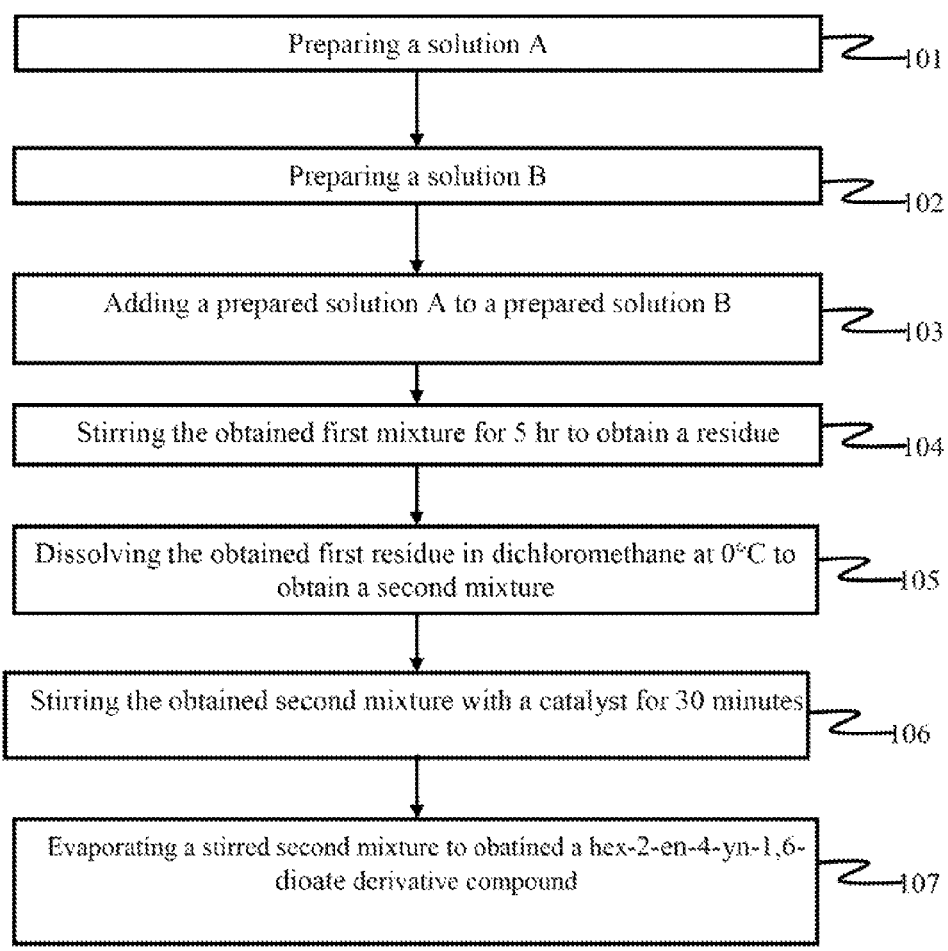
FIG. 1 shows a flow chart indicating the various steps involved in the synthesis of the hex-2-en-4-yn-1,6-dioate derivative compounds, according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide new chemical compounds and a method of synthesizing the new chemical compounds. The new chemical compounds are anti-fungal compounds.

The chemical compounds according to the embodiments herein have a property of inhibiting the production of aliphatic amino acids in fungal systems thereby inhibiting their growth. The mode of action and the inhibiting property of the newly developed antifungal compounds according to the embodiments herein, are determined through a reversal assay technique. In this assay the inhibitory effect of the antifungal compound is reversed by adding the different concentrations of various metabolic intermediates or building block molecules. In this way the inhibited metabolic pathway is recognized.

The embodiments herein provide a composition and a method of synthesizing a composition comprising an aliphatic amino acid biosynthesis inhibitor having an antifungal activity. According to one embodiment herein, an aliphatic amino acid biosynthesis inhibitor composition having an antifungal activity comprises a compound A, a compound B, a compound C and a compound D.

The compound A is 2-oxo-2H-chromen-7-yl propiolate and the compound 2-oxo-2H-chromen-7-yl propiolate is shown by formula (1)

$$\text{(1)}$$

The compound B is diethyl-hex-2-en-4-yne-dioate and the compound diethyl-hex-2-en-4-yne-dioate is shown by formula (2)

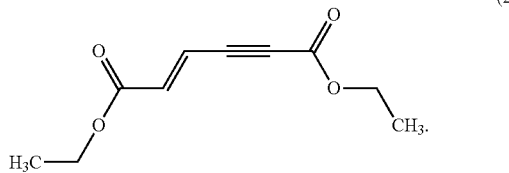

The compound C is dinonyl-hex-2-en-4-yne-dioate and the compound dinonyl-hex-2-en-4-yne-dioate is shown by formula (3)

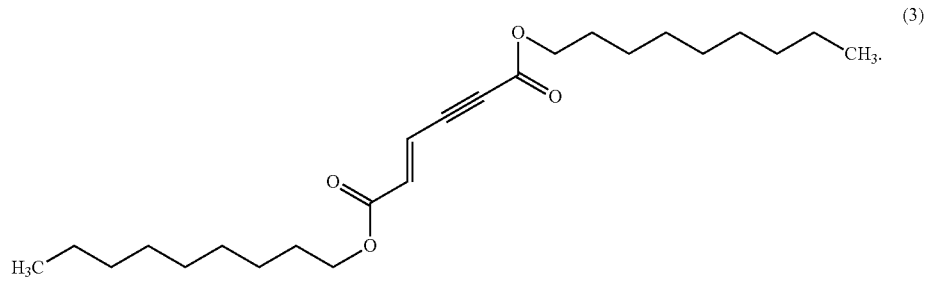 [SMILES: CCCCCCCCCOC(=O)C#C/C=C/C(=O)OCCCCCCCCC]

The compound D is shown by formula (4)

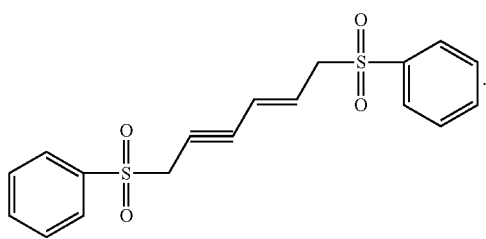

According to an embodiment herein, the composition inhibits a biosynthesis of an aliphatic amino acid in a fungal biological system. The aliphatic amino acid is selected from a group consisting of leucine, isoleucine and valine. The composition is used with a concentration of 0-200 µg/ml.

According to an embodiment herein, a method of synthesizing an aliphatic amino acid biosynthesis inhibitor composition having an antifungal activity. The method comprises preparing a solution A and a solution B. The solution A is prepared by mixing a compound E and a compound F. The compound E is dicyclohexylcarbodiimide (DCC) and the compound F is Dimethylaminopyridine (DMAP). The solution B is prepared by mixing a compound containing a hydroxyl group, an acetylene carboxylic acid and a solvent. The compound containing the hydroxyl group includes 7-hydroxy-chromen-2-one, ethanol and nonane-1-ol. The acetylene carboxylic acid is propiolic acid. The solvent is dichloromethane.

The prepared solution A is added to a prepared solution B at a predetermined temperature range drop wise over a predetermined time period to obtain a first mixture. The predetermined temperature range is 0° C.-4° C. and the predetermined time period is 1 hr. Further, the first mixture is stirred for a predetermined time to obtain a residue. The predetermined time is 5 hrs. The residue includes 2-oxo-2H-chromen-7-yl propiolate, ethyl propiolate, dodecyl propiolate and (Ethynylsulfonyl)benzene. The residue is dissolved in the solvent at a predefined temperature to obtain a second mixture. The solvent is dichloromethane. The predefined temperature is 0° C. The obtained second mixture is stirred with catalysts for a predefined time.

The catalysts include N,N'-Dicyclohexylcarbodiimide (DCC), 4-Dimethylaminopyridine (DMAP), and 1,4-diazabicyclo[2.2.2]octane (DABCO). The predefined time is 30 minutes. The stirred second mixture is evaporated to obtain a compound. The compound is hex-2-en-4-yn-1,6-dioate derivative compound.

The composition includes a compound A, a compound B, a compound C and a compound D. The compound A is 2-oxo-2H-chromen-7-yl propiolate and The compound 2-oxo-2H-chromen-7-yl propiolate is shown by formula (1)

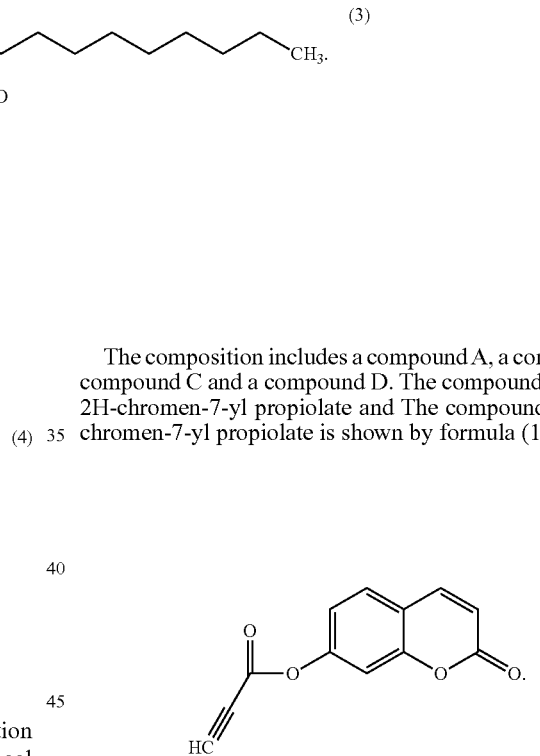

The compound B is diethyl-hex-2-en-4-yne-dioate and the compound diethyl-hex-2-en-4-yne-dioate is shown by formula (2)

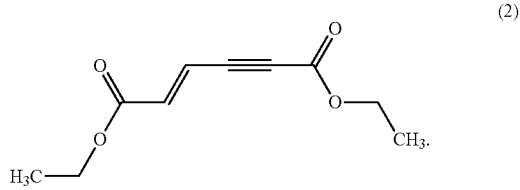

The compound C is dinonyl-hex-2-en-4-yne-dioate and the compound dinonyl-hex-2-en-4-yne-dioate is shown by formula (3) mixture with ether and further evaporating till the residue is obtained (104). The obtained residue is dissolved in dichloromethane at 0° C. to obtain a second mixture (105).

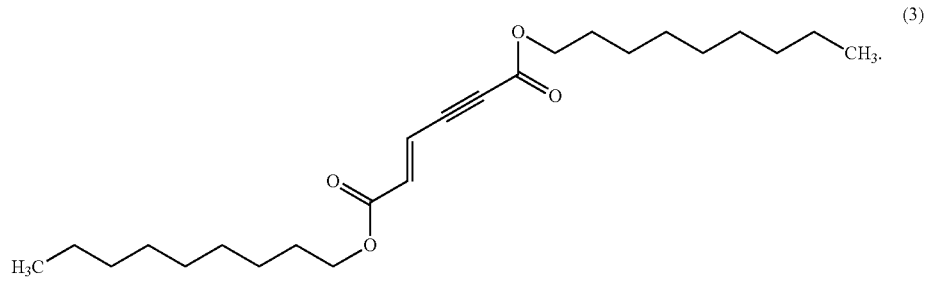 [SMILES: CCCCCCCCCOC(=O)C#C/C=C/C(=O)OCCCCCCCCC]

(3)

The compound D is shown by formula (4)

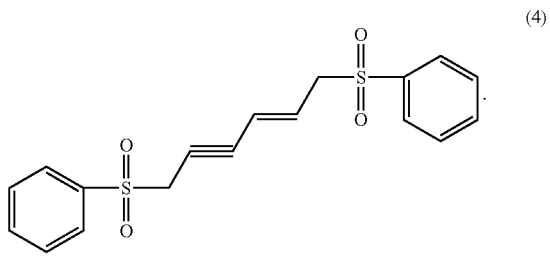 [SMILES: O=S(=O)(CC#C/C=C/CS(=O)(=O)c1ccccc1)c1ccccc1]

(4)

The composition inhibits a biosynthesis of an aliphatic amino acid in a fungal biological system. The amino acid is selected from a group consisting of leucine, isoleucine and valine. The composition is used with a concentration of 0-200 µg/ml.

According to an embodiment herein, a method of synthesizing a compound comprising a chemical moiety of -hex-2-en-4-yn-1,6-dioate. The chemical moiety according to the embodiments herein has antifungal activity.

The chemical moiety is capable of inhibiting the production of necessary amino acids in the biochemical cycles of the fungal pathogens.

According to an embodiment herein, the method for detecting the mechanism of action of compounds is the reversal assay technique. The mechanism of the synthesis of antifungal compounds that provide resistance to an antifungal drug in fungal system is provided. Indeed, the pathway through which the drug is inhibited is defined by this way. According to another embodiment herein, the effect of the synthesized antibiotics on the biosynthetic amino acids, nucleic acids and citric acid cycle is provided.

FIG. 1 shows a flow chart indicating the various steps involved in the synthesis of the hex-2-en-4-yn-1,6-dioate derivative compounds, according to an embodiment herein. With respect to FIG. 1, a solution A is prepared. The solution A is prepared by mixing dicyclohexylcarbodiimide (DCC) and a Dimethylaminopyridine (DMAP) (101). Then a solution B is prepared. The solution B is prepared by mixing an alcohol and an acetylene carboxylic acid with dichloromethane (102). The prepared solution A is added to a prepared solution B. The prepared solution A is added to a prepared solution B at 0° C. to 4° C. drop wise over a period of 1 hr to obtain a first mixture (103). The obtained first mixture is stirred for 5 hrs to obtain a residue. The residue is obtained by filtering the first mixture. Then washing the first The obtained second mixture is stirred with a catalyst for 30 minutes (106). The stirred second mixture is evaporated to obtained a hex-2-en-4-yn-1,6-dioate derivative compound (107). The compound is further purified with a silica gel column chromatography method.

According to an embodiment herein, the dicyclohexylcarbodiimide (DCC) is mixed with a concentration of 9.25 mmol. The Dimethylaminopyridine (DMAP) is mixed with a concentration of 0.011 mmol. The alcohol is selected from a group consisting of ethanol and nonane-1-ol. The alcohol is mixed with a concentration of 10 mmol. The acetylene carboxylic acid is mixed with a concentration of 9.25 mmol. The first residue is selected from a group consisting of ethyl propiolate, dodecyl propiolate and phenyl sulfone propiolate. The catalyst includes N,N'-Dicyclohexylcarbodiimide (DCC), 4-Dimethylaminopyridine (DMAP) and 1,4-diazabicyclo[2.2.2]octane (DAB CO). The 1,4-diazabicyclo[2.2.2]octane (DABCO) is used with a concentration of 0.05 mmol.

The embodiments herein are supported with following examples. The examples set forth are not meant to limit the scope in any manner.

EXAMPLE 1

The new chemical compound is synthesized by a method comprising the steps of mixing a 9.25 mmol solution of dicyclohexylcarbodiimide (DCC) and 0.011 mmol of Dimethylaminopyridine (DMAP) with a solution containing 10 mmol of 7-hydroxy-2H-chromen-2-one, 9.25 mmol of propiolic acid and 5 ml of dichloromethane. The solutions are mixed at a temperature range of 0° C.-4° C. over a period of 1 hr. The mixture is stirred for additional 5 hrs. The mixture is then filtered and washed with ether. The mixture is evaporated to obtain a product. The product is purified using a silica gel chromatography. The synthesized new chemical compound is 2-oxo-2H-chromen-7-yl propiolate:

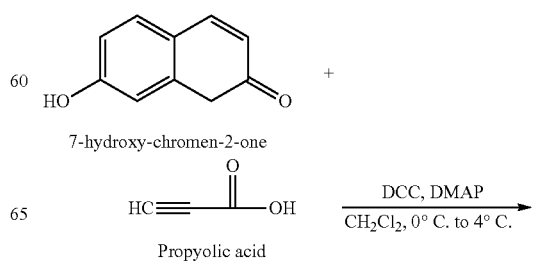

-continued

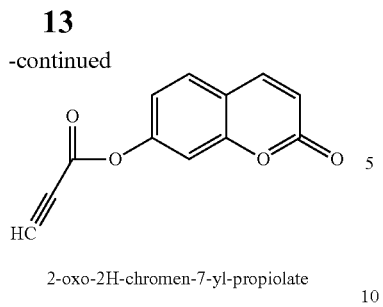

2-oxo-2H-chromen-7-yl-propiolate

EXAMPLE 2

The new chemical compound is synthesized by a method comprising the steps of mixing a 9.25 mmol solution of dicyclohexylcarbodiimide (DCC) and 0.011 mmol of Dimethylaminopyridine (DMAP) with a solution containing 10 mmol of ethanol, 9.25 mmol of propiolic acid and 5 ml of dichloromethane. The solutions are mixed at a temperature range of 0° C.-4° C. over a period of 1 hr. The mixture is stirred for additional 5 hrs to form an intermediate. The formed intermediate is ethyl propiolate. The ethyl propiolate is dissolved in 5 ml of dichloromethane at 0° C. Then the mixture is stirred for 30 minutes in the presence of 0.05 mmol of 1,4-diazabicyclo[2.2.2]octane (DABCO) which acts as a catalyst. The volatiles are evaporated and the crude reaction mixture is purified by silica gel chromatography. The synthesized new chemical compound is diethyl-hex-2-en-4-yne-dioate:

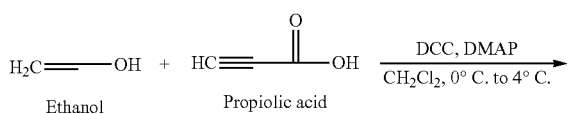

Ethanol    Propiolic acid

-continued

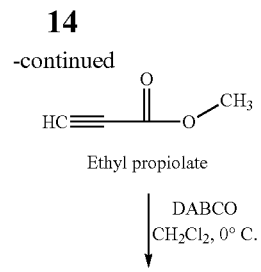

Ethyl propiolate

↓ DABCO
CH$_2$Cl$_2$, 0° C.

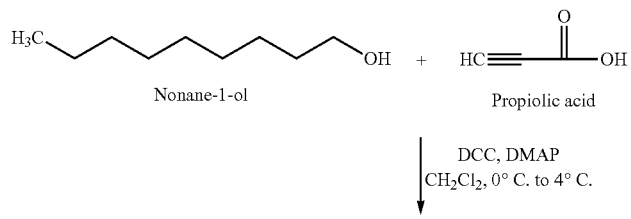

Diethyl-hex-2-en-4-yne-dioate

EXAMPLE 3

The new chemical compound is synthesized by a method comprising the steps of mixing a 9.25 mmol solution of dicyclohexylcarbodiimide (DCC) and 0.011 mmol of Dimethylaminopyridine (DMAP) with a solution containing 10 mmol of nonan-1-ol, 9.25 mmol of propiolic acid and 5 ml of dichloromethane. The solutions are mixed at a temperature range of 0° C.-4° C. over a period of 1 hr. The mixture is stirred for additional 5 hrs to form an intermediate. The formed intermediate is dodecyl propiolate. The dodecyl propiolate is dissolved in 5 ml of dichloromethane at 0° C. Next the mixture is stirred for 30 minutes in the presence of 0.05 mmol of 1,4-diazabicyclo[2.2.2]octane (DABCO) which acts as a catalyst here. The volatiles are evaporated and the crude reaction mixture is purified by silica gel chromatography. The synthesized new chemical compound is dinonyl-hex-2-en-4-yne-dioate.

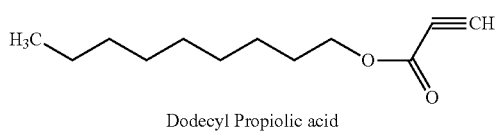

Nonane-1-ol    Propiolic acid

↓ DCC, DMAP
CH$_2$Cl$_2$, 0° C. to 4° C.

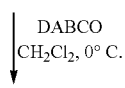

Dodecyl Propiolic acid

↓ DABCO
CH$_2$Cl$_2$, 0° C.

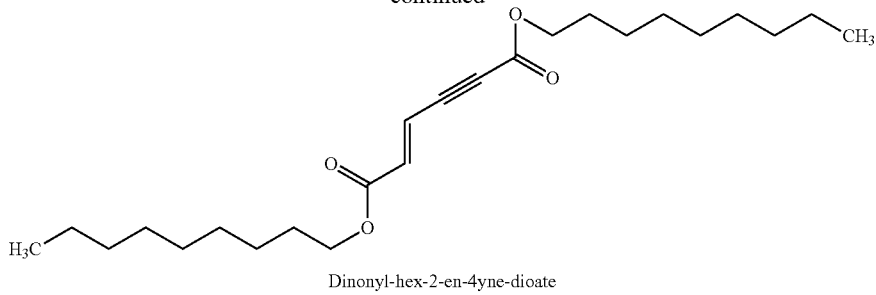

Dinonyl-hex-2-en-4yne-dioate

EXAMPLE 4

The compound D is synthesized by the same method as mentioned in Example 2, 3 and 4:

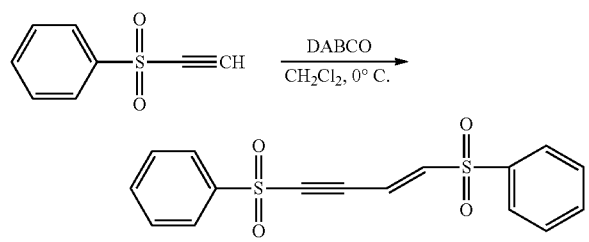

The newly synthesized compounds according to the embodiments herein are different from the existing anti-fungal compounds. The existing anti-fungal compound such as Terbinafine is an acetylenic compound that is obtained from modification of naftifine. The variations of the naftifine molecule showed that the antifungal activity was specially linked to certain structural elements. Those certain structural elements could not be related with the structural elements of the newly synthesized antifungal agents according to the embodiment herein. The newly synthesized agents do not have the tertiary allyamine moiety as present in the existing anti-fungal drugs. The other antifungal drugs like azoles contain the triazol moiety which is absent in the newly synthesized compounds according to the embodiments herein. Another anti-fungal agent named Amphotericin B is a cyclic compound with a conjugated double bond which is a totally different structure from the structures of the newly synthesized compounds according to the embodiments herein. Thus the newly synthesized compounds are novel and have a totally different structure. The newly developed compounds have triple bond in conjugation with double bond which is believed to be the reason for their anti-fungal activity. The in silico study is used to predict whether a compound with a triple bond can posses antifungal activity with a reasonable prediction probability or not. In addition to the above, a preliminary study on the effect of triple bond position compared to other functional groups is provided. According to the in silico study, the presence of triple bond in conjugation with a double bond is very important to provide anti-fungal activity.

EXPERIMENTAL DATA

Performing reversal assay: The reversal assay according to the embodiments herein is performed by the following steps in general: First the yeast strain is grown in presence of minimum inhibitory concentrations of the compounds to be tested. Then different concentrations of amino acids or metabolite intermediates are added to reverse the inhibitory effect of the test compounds. Then again the growth is checked and the minimum concentration of the metabolite or amino acids required for reversing the inhibitory effect is determined.

According to the embodiments herein, the new developed compounds are named as compound A, compound B, compound C and compound D as shown:

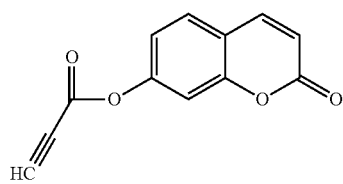

Compound A (Test Compound)

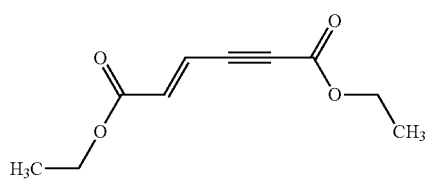

Compound B

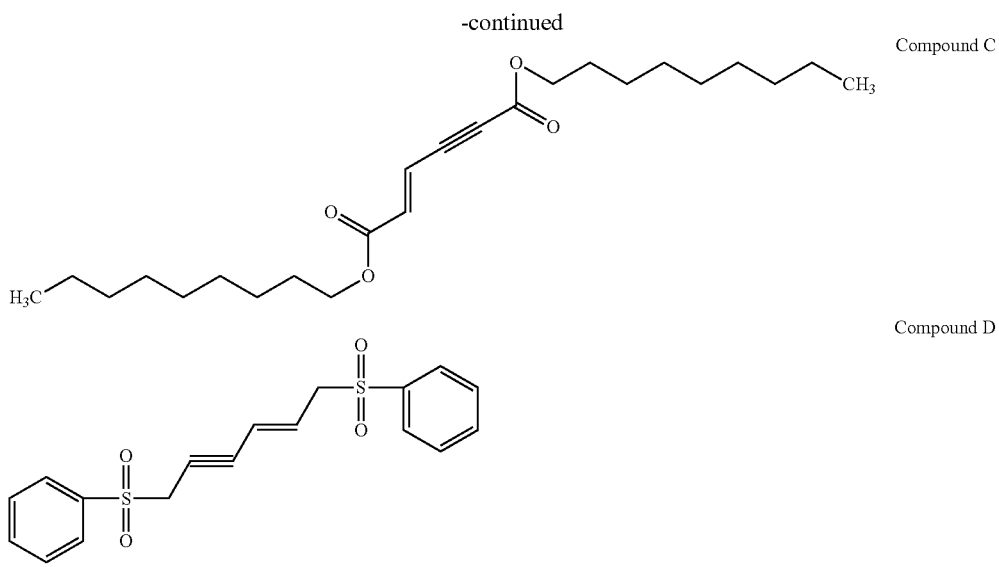

Compound C

Compound D

Synthesis of the Compounds:

A 9.25 mmol solution of dicyclohexylcarbodiimide (DCC) and 0.011 mmol of Dimethylaminopyridine (DMAP) was added to a solution containing a compound derivate of hydroxyl group. The compound derivate of hydroxyl group is 7-hydroxy-chromen-2-one (for compound A), ethanol (for compound B) and nonan-1-ol (for compound C) with 10 mmol concentration, in acetylene carboxylic acid or 9.25 mmol of propiolic acid and 5 ml of dichloromethane ($CH_2Cl_2$) at 0° C. to 4° C. over a period of 1 h. The reaction was stirred for an additional 5 h. Then the mixture was filtered and washed with ether. Following an evaporation of the solvents the product was purified using a silica gel chromatography. At this stage compound A (2-oxo-2H-chromen-7-yl propiolate), ethyl propiolate and dodecyl propiolate were obtained (Reaction 1-a).

To complete the procedure and for the synthesis of compound B and C, the ethyl propiolate and nonyl propiolate that obtained from the last stage were dissolved in 5 ml of dichloromethane ($CH_1Cl_1$) at 0° C. Then the mixture was stirred for 30 minutes in the presence of 0.05 mmol of 1,4-diazabicyclo[2.2.2]octane (DABCO) acting as a catalyst. The volatiles were evaporated and the crude reaction mixture was purified by a silica gel chromatography (Reaction 1-b).

Also for synthesis compound D, this method was used as shown in Reaction 1-c:

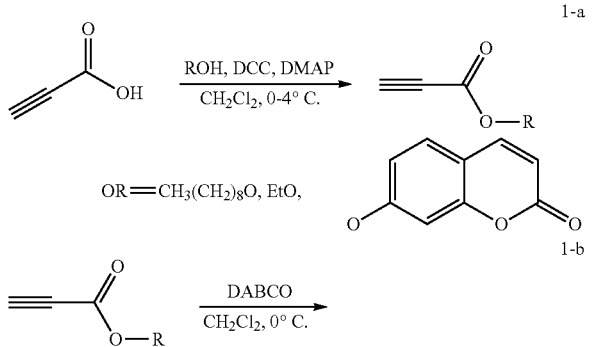

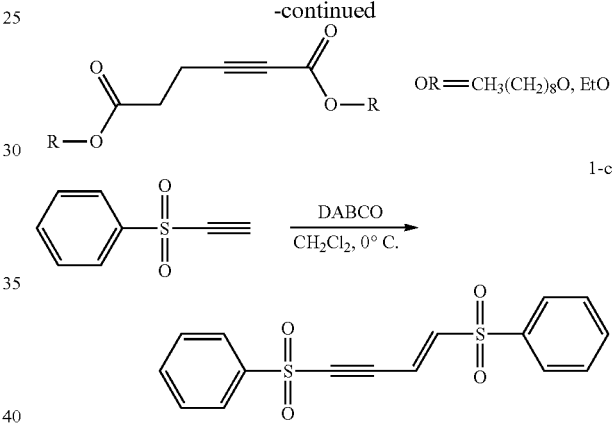

Antifungal Activity and Determining the Minimum Inhibitory Concentration of the Newly Synthesized Compounds:

For finding an answer for the question that the presence of which amino acids, nucleotide and the mediating products of citric acid cycle, the materials were examined for observing the effect of intended antibiotics in the presence of microorganisms.

To achieve this, firstly the Minimum Inhibitory Concentration (MIC) of the new developed compounds according to the embodiments herein was determined and then reversal assay was implemented separately. The compounds were: compound A as test compound and compound B as main compound. Compound A is renamed to test compound in the description of the specification in order to prevent confusion. A test compound can be used as a control. It contains certain elements of the main compound such as compound B. However the structural features and bioactivity lacks the reversal property.

Two fold serial dilutions of the compounds to be tested according to the embodiments herein were prepared in 96 well plates. 40 µl of appropriate test compound dilution was added to 160 µl of culture medium and the plate was incubated at 30° C. The culture medium is Yeast Peptone Dextrose agar (YPD) containing $10^3$ yeast cells. The growth of yeast cells was monitored for 24 hr and 48 hr. Fluorouracil was used as a positive control and Dimethyl sulfoxide (DMSO-control solvent) was used as negative control. The minimum concentration of the test compound A which inhibits the fungal growth was defined as MIC. MIC level is defined as the minimum concentration of the compound which prevents the growth of pathogen. According to the embodiments herein the pathogen is fungus.

Further, after counting the cells by neobar 1am, 100 µl of sterile water was poured into all of the wells of the second row and then 60 µl or more water was added to the well number 1 of the second row to get water with the volume of 160 µl. Then 40 µl of the test compound with a concentration/dilution of 5 mg/ml was added to 160 µl of water in the first well and to get a final volume of 200 µl in this well. Then 100 µl of this well was taken by a sampler and added to the second well. After 2-3 times of pipeting, 100 µl was added to the third well. This was continued to well 11 that 100 µl of that was taken and thrown away.

After providing a serial dilution in the second row, 20 µl of the wells of the second row was transformed to the wells of first row and final volume of the wells of first row was changed to 100 µl. Finally, a surrounding part of each plate was covered with parafilm and was incubated under 37 degree of centigrade. the results were read out After 24 hours and 48 hours. The same was done for row 3 and row 4 for fluorouracil drug which is used as control drug and row 5 and row 6 for DMSO which is used as control solvent.

Defining the MIC of the Compounds:

As a result of the growth of the fungus the medium is becoming cloudy. The growth of the fungus can be studied by comparing the tiff with the first sample and the sample which is the result of 24 hours and 48 hours incubation. Minimum Inhibitory Concentration (MIC) is the minimum concentration of antifungal substance that avoids the fungal growth. For defining the MIC, as well as the sample, positive control i.e. an approved antifungal drug like fluorouracil were measured. A solution control and a negative control i.e. only the fungal suspension were measured. The growth of the fungus in the presence of tested compounds was compared with the growth of the fungus in positive control.

Figure 2:
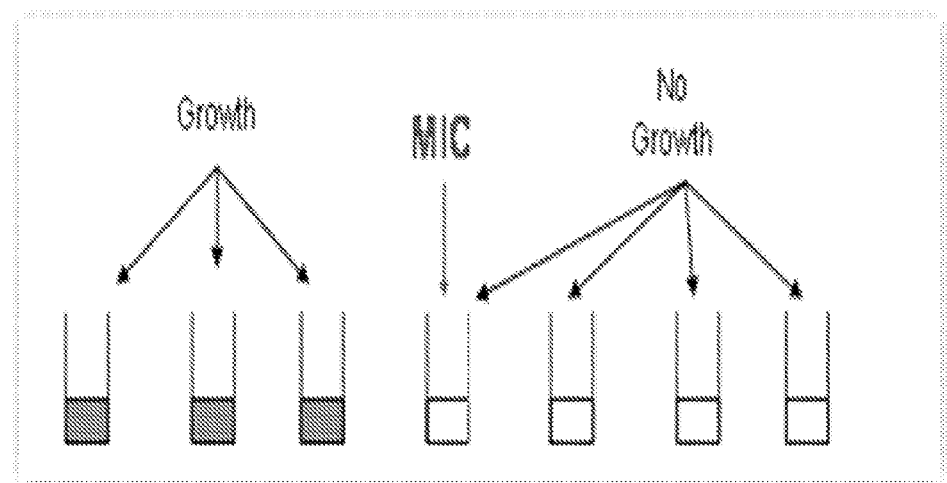
FIG. 2 illustrates a schematic representation of a process for determining a Minimum Inhibitory Concentration (MIC) of the hex-2-en-4-yn-1,6-dioate derivative compounds in preventing a growth of a pathogen such as fungus, according to an embodiment herein.

FIG. 2 illustrates a schematic representation of a process for determining a Minimum Inhibitory Concentration (MIC) of the hex-2-en-4-yn-1,6-dioate derivative compounds in preventing a growth of a pathogen such as fungus, according to an embodiment herein. With respect to FIG. 2, the growth was observed in the initial three wells counted from a left hand side. No growth was observed in the forth well that is the well having a minimum Inhibition concentration of the sample.

Figure 3:
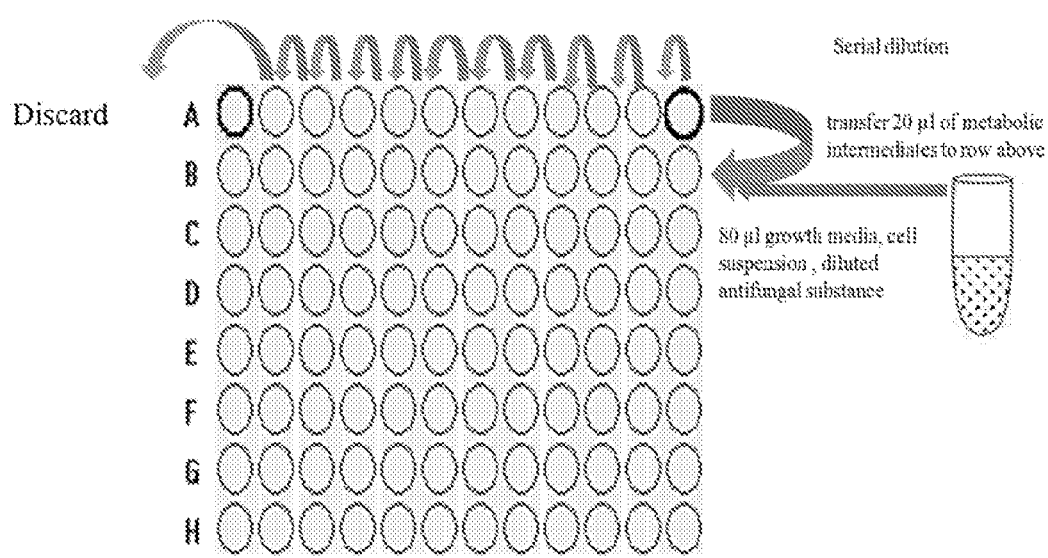
FIG. 3 shows a schematic representation of a reversal assay method for finding any metabolite in hex-2-en-4-yn-1,6-dioate derivative compounds to reverse antifungal activity, according to one embodiment herein.

Implementing the Reversal Assay Test:

An experiment was designed for finding the metabolite that reverses the antifungal activity of the test compound. FIG. 3 shows a schematic representation of a reversal assay method for finding any metabolite in hex-2-en-4-yn-1,6-dioate derivative compounds to reverse antifungal activity, according to one embodiment herein.

With respect to FIG. 3, a cell suspension containing 1.5× $10^5$ yeast/ml was prepared in RPMI medium (1.2×) enriched by 2% glucose. An appropriate amount of antifungal compound B was added to the cell suspension to provide the MIC level of the compound. Compound B with 1.5 µg/ml concentration was added. 80 µl of this suspension was added to each well of a 96 well micro plate in the second row. Subsequently, two fold dilutions of reversing metabolite were prepared in the first row of the same microplate and 20 µl of each dilution was added to the related well of the second row. The plate was incubated at 30° C. overnight. Following an overnight incubation, the plate was checked for any visible growth of the strain. In case of any growth, the reversing metabolite was considered for further analysis.

In this test, all the amino acids, nucleic acids and intermediate metabolites of citric acid cycle were tested separately.

Further, thin layer chromatography (TLC) was used to roll out any inhibitory interaction between the antifungal compound B and each of reversing amino acids. Any physical interaction of test compound A and amino acids which could prevent the compound B to enter the cell was analysed.

Thin Layer Chromatography:

Thin layer chromatography is a kind of absorptive solid-liquid chromatography. A drop of sample or solvent is situated near the edge of chromatogram plate covered by a special separation matrix like silica gel. The plate is then placed inside a chamber containing an appropriate amount of an eluent solvent. During the chromatography, the solvent moves toward the highest point of the silica gel plate and separates the components of the mixture with different rates. Finally the separated compounds are visualized by staining or direct observation under Ultra Violate (UV) light.

To complete the experiment, the silica gel plate is taken out and dried and the separated spots (components) are visualized. In the embodiments herein, the synthetic compound B was detected using a UV lamp. However amino acids were visualized by staining with ninhydrin reagent. The plate was sprayed with a ninhydin solution and heated for 5 minutes to develop the spots. A ninhydrin base indicator was sprayed on the chromatogram after implementing TLC and a red stain (acid amine) appeared after being situated on the heater for 5 minutes.

Figure 4:
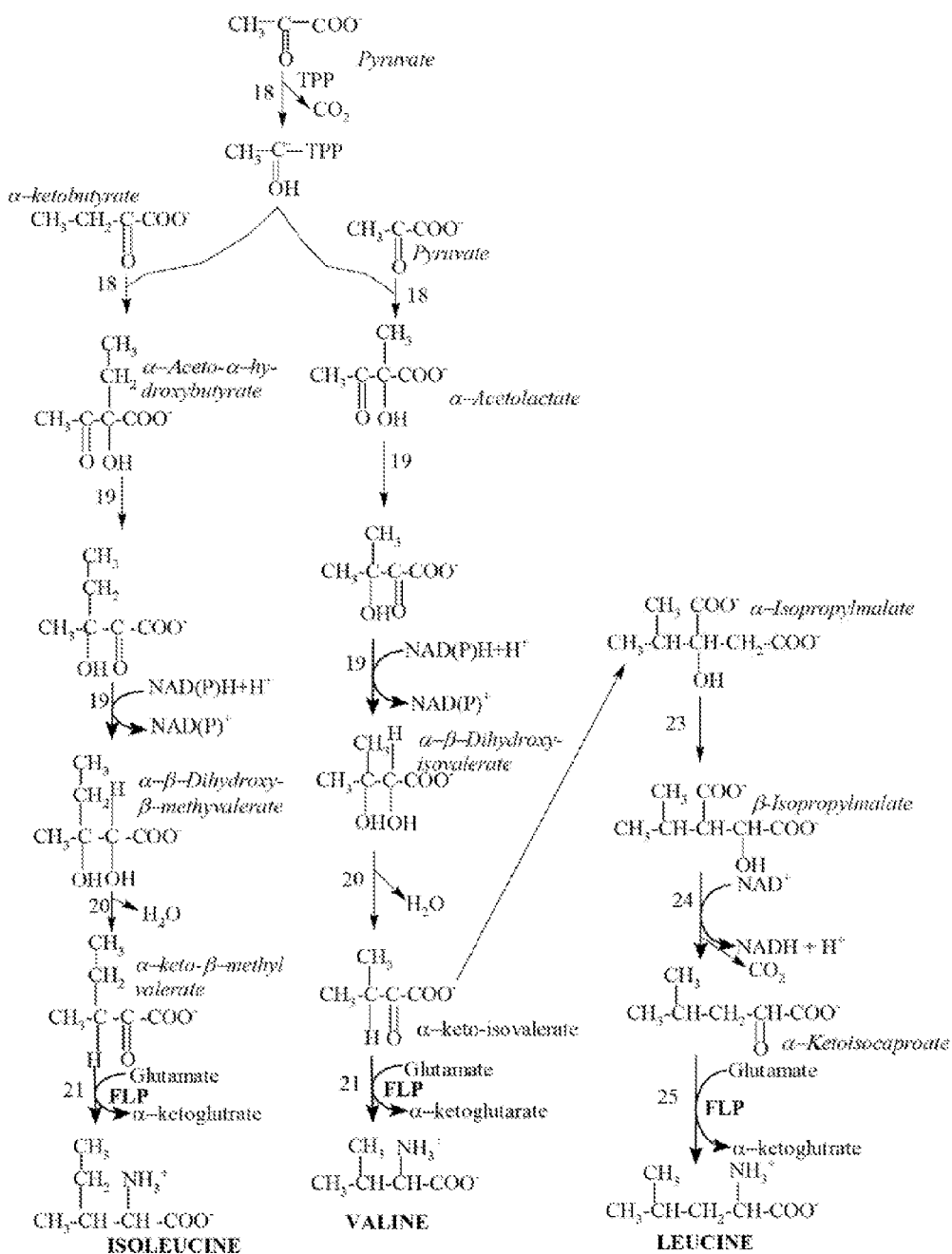
FIG. 4 shows a biosynthetic pathway of branched amino acids in yeast *Saccharomyces cerevisiae* indicating the pathway for the production of the branched amino acids that are leucine, isoleucine, and valine, according to one embodiment herein.

Branched Chain Amino Acids Biosynthetic Pathway:

FIG. 4 shows a biosynthetic pathway of branched amino acids in yeast *Saccharomyces cerevisiae* indicating the pathway for the production of the branched amino acids that are leucine, isoleucine, and valine, according to one embodiment herein.

With respect to FIG. 4, a biosynthetic pathway of branched amino acids in yeast *Saccharomyces cerevisiae* indicates the pathway for the production of the branched amino acids such as leucine, isoleucine, and valine. As it is shown in FIG. 4, the biosynthesis of leucine, isoleucine and valine share common steps in yeast *Saccharomyces cerevisiae*. The three enzymes: acetolactate synthase (ILV2) acetohydroxy acid isomeroreductase (ILV5) and dihydroxy acid dehydratase (ILV3) catalyses the common primary steps in the branched amino acid biosynthesis pathway. The valine and isoleucine pathways share four enzymes. Pyruvate gives rise to valine and isoleucine in pathways begin with a condensation of two pyruvate carbons (in the form of hydroxyethyl thiamine pyrophosphate) with another molecule of pyruvate (valine path) or with α-ketobutyrate (isoleucine path). The α-ketobutyrate is derived from threonine in a reaction that requires pyridoxal phosphate. An intermediate product in the valine pathway, α-ketoisovalerate, is the starting point for a four-step branch pathway leading to leucine.

The sequences of these three genes were downloaded from the *Saccharomyces* genome database (SGD) website at www.SGD.com and the gene specific primers were designed accordingly. The expression levels of candidate genes were analyzed for the presence and absence of synthetic antifungal compound.

Semi-Quantified RT-PCR:

A semi quantitative RT-PCR analysis was used to investigate any possible effect of new antifungal compounds on the expression level of candidate gene targets.

RNA Preparation:

The RNA samples were prepared by using a commercial kit i.e. RNA easy mini kit, QIAGEN, Germany. A beads cell disrupter i.e. Micro Smash™, Tomy, Japan was used during the cell lysis process. All RNA preparation steps were performed according to the manufacturer's instructions.

cDNA Synthesis Reaction:

1 microgram of total RNA was used in cDNA synthesis reaction. A commercial kit i.e. first strand cDNA Synthesis Kit, Fermentas, USA was used for cDNA synthesis. Total cDNA was prepared using random hexamer primer and all steps were according to the manufacturer's instructions. A typical reaction was performed as table 1 below.

TABLE 1

SHOWING cDNA SYNTHESIS REACTION MIXTURE

| Material | Amount |
| --- | --- |
| Total RNA | 3 µL |
| Random hexamer | 1 µL |
| DEPC-treated water | 9 µL |
| 5X reaction buffer | 4 µL |
| RiboLockTMTibonuclease Inhibitor | 1 µL |
| 10mMdNTP mix | 2 µL |
| M-MuLV reverse transcriptase | 1 µL |

Following cDNA synthesis, the synthesized cDNA was used in RT-PCR reaction. Table 2 shows the sequence of specific primers used in RT-PCR reaction.

TABLE 2

SHOWING THE PRIMERS USED IN RT-PCR REACTION

| Name of the primer | Primer Sequence |
| --- | --- |
| ILV5-F | 5'-CTATCAAGAG AGGTAGTTAC-3' |
| ILV5-R | 5'-TAACCGGAACCAATGGCAAC-3' |
| ILV2-F | 5'-GTGACCGTGC TCAAATACCT-3' |
| ILV2-R | 5'-ACGGTCGTCGAATCTAGCAC-3' |
| ILV3-F | 5'-AACCGGTGGGTCCACTAATG-3' |
| ILV3-R | 5'-CATGTTGCACGGTAACAC-3' |
| ACT-F | 5'-GGTTATTGATAACGGTTCTG-3' |
| ACT-R | 5'-GGGCAACTCTCAATTCGTTG-3' |

RT-PCR Analysis:

RT-PCR analysis was carried out to examine the effect of new antifungal compounds on the expression level of genes involved in aliphatic amino acids biosynthesis. Three genes, ilv2, ilv3 and ilv5 were chosen for further analysis. RNA samples were isolated from the yeast cells exposed to sublethal or sub-inhibitory concentrations of new antifungal compounds and following a cDNA preparation. RT-PCR was performed using the gene specific primers. Table 3 demonstrates a typical RT-PCR reaction used in an expression analysis.

TABLE 3

SHOWING AN EXAMPLE OF RT-PCR REACTION

| Type of the required material | Amounts |
| --- | --- |
| Master mix | 12/5 µL |
| Reverse primer | 1 µL (5 pmol) |
| Forward primer | 1 µL (5 pmol) |
| cDNA | 1 µL (200 ng) |
| dH2O | 9/5 µL |
| Total Volume | 25 L |

The Analysis of the RT-PCR Products:

RT-PCR products were visualized by electrophoresis on agarose gel and staining by ethidium bromide.

The Interaction Between Antifungal Synthetic Compound and ILV5 Enzyme (Acetohydroxyacid Reductoisomerase) at the In Silico Environment:

Docking is a technique that virtually investigates with the level of the tendency and interaction between two molecules (ligand-receptor) at the in silico environment. For this to be done, the Arguslab software was used. Arguslab is a graphic program and one of its special features is that it can calculate and can three dimensionally illustrate the different possible modes of molecule interactions.

Antifungal compound synthesized according to the embodiments herein was considered as ligand and acetohydroxyacid reductoisomerase was considered as receptor. For performing a docking, the intended compound was drawn using Marvin software and also minimization was carried out with the same software. Amino acids existing in the active site of the enzyme were located in the box by the available tools of the software. Hence docking is done in this region and investigation was performed locally. In this application, two algorithms called Genetic Algorithm, GA and ArgusLab Dock can be used. For inputting the files, different formats such as PDB, Mol, Mol2, etc can be used.

RESULTS

Figure 5:
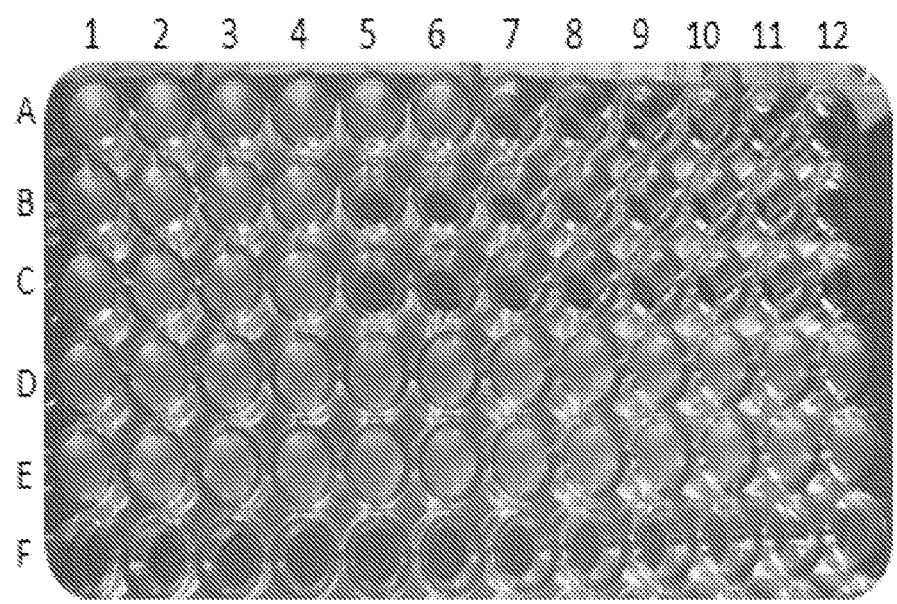
FIG. 5 shows a schematic representation of an assay for a determination of Minimum Inhibitory Concentration (MIC) of the antifungal activity of the hex-2-en-4-yn-1,6-dioate derivative compounds, according to one embodiment herein.

Results Related to the Determination of Minimum Inhibitory Concentration:

The investigation of antifungal activity and MIC of synthetic antifungal compounds with micro serial dilution method in 96 well plate after 48 hours incubation is presented in FIG. 5.

FIG. 5 shows a schematic representation of an assay for a determination of Minimum Inhibitory Concentration (MIC) of the antifungal activity of the hex-2-en-4-yn-1,6-dioate derivative compounds, according to one embodiment herein. With respect to FIG. 5, Row A shows the yeast cells grown in the presence of different concentrations of the test compound. The test compound has a concentration range of 0-200 µg/ml. The Row B shows the yeast cells grown in the presence of different concentrations of compound B. The concentration of compound B is within a concentration range of 0-200 µg/ml. The Row C shows the yeast cells grown in the presence of different concentrations of a positive control compound such as fluorouracil. The fluorouracil is used with a concentration range of 0-200 µg/ml. Row D shows the yeast cell growth in well containing cell control i.e. containing the medium and the yeast. The Row E contains DMSO solvent control (% v/v) and Row F is medium control containing the medium only. As it is seen in FIG. 5, MIC of the compounds is 1.5 µg/ml. Other synthesized compounds were tested and for the mechanistic studies, only compound B was chosen.

Results of Reversal Assay Test:

For all the compounds the mixture of mediators was evaluated. After observing that the compound was reversed, each of the mediating materials was tested separately. Reversal assay test has been done for all of the amino acids like glycine, alanine, leucine, isoleucine and valine. The Reading of reversal assay test related to compound B on all the amino acids such as valine, glycine, alanine, leucine and isoleucine are presented in FIG. 6.

Figure 6:
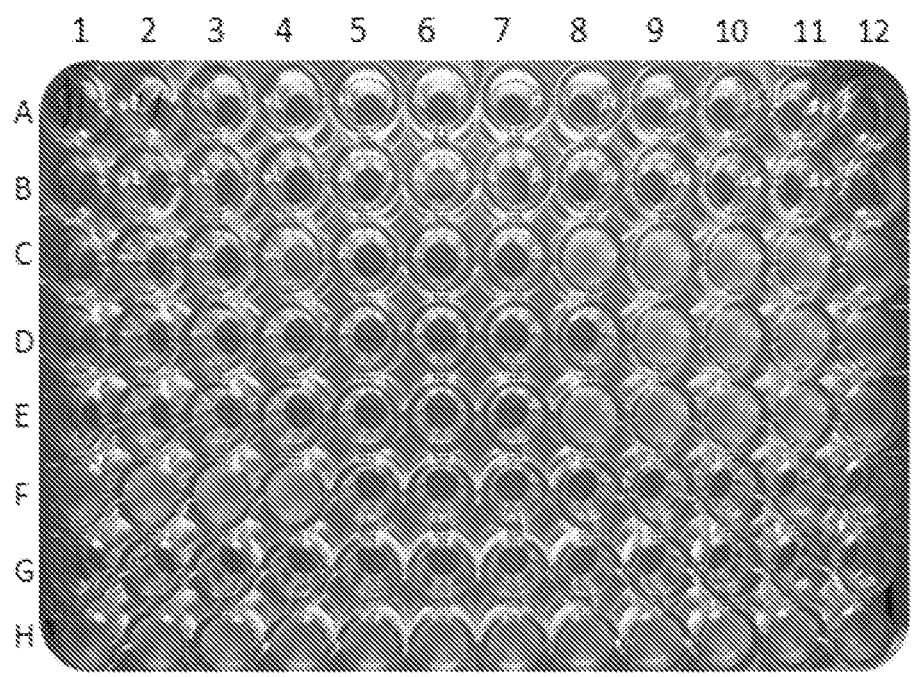
FIG. 6 shows a schematic representation of a Reversal assay test related to a compound B on amino acids such as alanine, glycine, leucine, isoleucine and valine amino acids, according to one embodiment herein.

FIG. 6 shows a schematic presentation of a Reversal assay test related to a compound B for alanine, glycine, leucine, isoleucine and valine amino acids, according to the embodiments herein. With respect to FIG. 6, Row A indicates a result of a reversal assay at a concentration range of 0-200 µg/ml of alanine amino acids in compound B with a constant concentration of MIC level. Row B indicates a result of a reversal assay at a concentration range of 0-200 µg/ml of glycine amino acids in compound B with a constant concentration of MIC level. Row C indicates a result of a reversal assay at a concentration range 0-200 µg/ml of leucine amino acids in compound B with a constant concentration of MIC level. Row D indicates a result of a reversal assay at a concentration range 0-200 µg/ml of isoleucine amino acids in compound B with a constant concentration of MIC level. Row E indicates a result of is reversal assay at concentration range 0-200 µg/ml of valine amino acids in constant concentration of compound B at MIC level. Row F indicates a result of defining MIC from compound B with a concentration of 0 to 200 µg/ml. Row G indicates a compound B in the absence of amino acids and cells. Row H is control cell.

As shown in FIG. 6, the growth was observed in row C that is related to leucine amino acid, row D that is isoleucine amino acid and row E that is valine amino acid. The amount of Minimum Reversal Concentration (MRC) related to these amino acids is equal to 12.5 µg/ml, 25 µg/ml and 12.5 µg/ml, respectively. The Minimum Reversal Concentration (MIC) is a concentration of the intermediate or the cellular metabolite which reverses the inhibitory action of the drug or the active compound at its Minimum Inhibitory Concentration (MIC) level.

Figure 7:
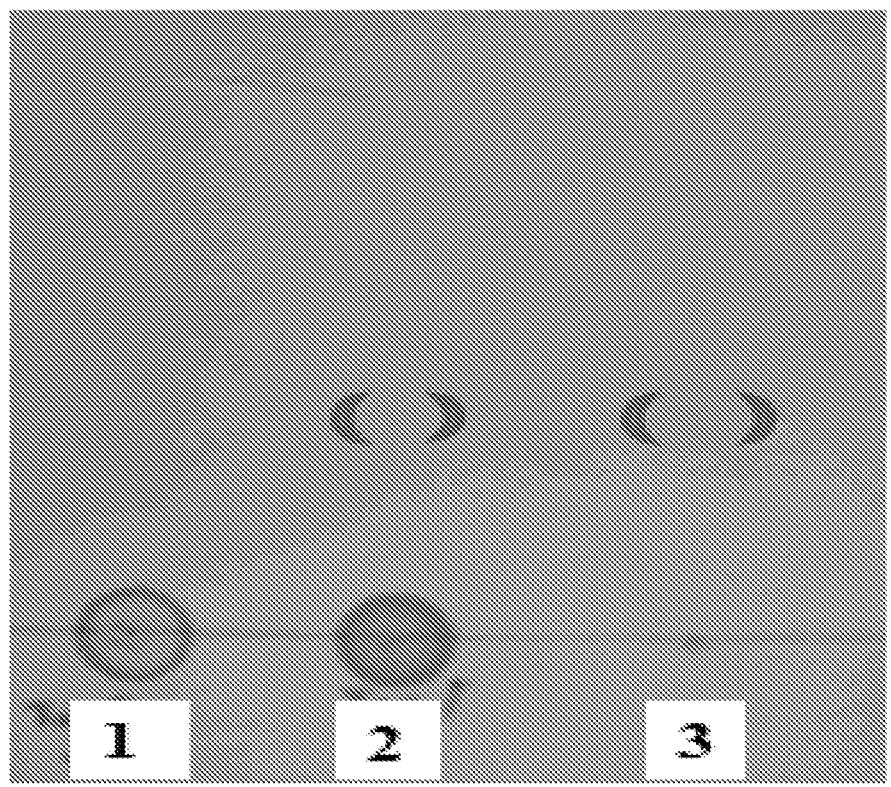
FIG. 7 shows a Thin Layer Chromatography plate illustrating the separated stains using ninhydrin solution for amino acids, antifungal compound with amino acids and the synthesized anti-fungal compound, according to the embodiments herein.

Results of Thin Layer Chromatography (TLC):

The ninhydrin indicator was used for revealing the amino acid spots after the implementation of TLC. FIG. 7 shows a Thin Layer Chromatography plate illustrating the separated stains using ninhydrin solution for amino acids, antifungal compound with amino acids and the synthesized anti-fungal compound, according to the embodiments herein.

With respect to FIG. 7, the point (1) shows the stain for amino acids, the point (2) shows the stain for amino acids and antifungal compound B and the point (3) shows the stain for the antifungal compound B. The blue brackets show the position of the compound B as it is seen under the UV light. The red stains are amino acid spots. The bracket marks as shown by the blue color were the locations in which antifungal compound B spots were observed by UV lamp and were marked.

As shown in FIG. 7, the amino acid spot was totally separate from the antifungal compound. Therefore, it can be said that this compound does not have an interaction with leucine, isoleucine and valine amino acids.

the Expression Analysis of ILV5 in Presence or Absence of New Antifungal Compound:

The enzyme ILV5 is not present in humans and animals and as a result, the inhibition of the enzyme activity with the synthesized compound according to the embodiments herein or similar compounds does not affect a human health and only targets the fungal pathogen. This means that the newly synthesized compounds are specific for a fungi or for the organisms that have a similar pathway for biosynthesis of aliphatic amino acid.

An overnight culture of yeast *Saccharomyces cerevisiae* BY4741 was prepared. A day after, 2×50 ml of YPD medium was inoculated with $10^5$ yeast/ml and the cultures were shaken at 250 rpm in 30° C. for 2 hours. After 2 hours of incubation, a sub-lethal dose of antifungal compound B was added to the test culture and the same amount of drug solvent was added to the control cultures. All the experiments were carried out in triplicates. The incubation of test and control cultures was continued for another 4 hours. Subsequently, the cells were harvested and subjected to RNA extraction and RT-PCR analysis.

Figure 8:
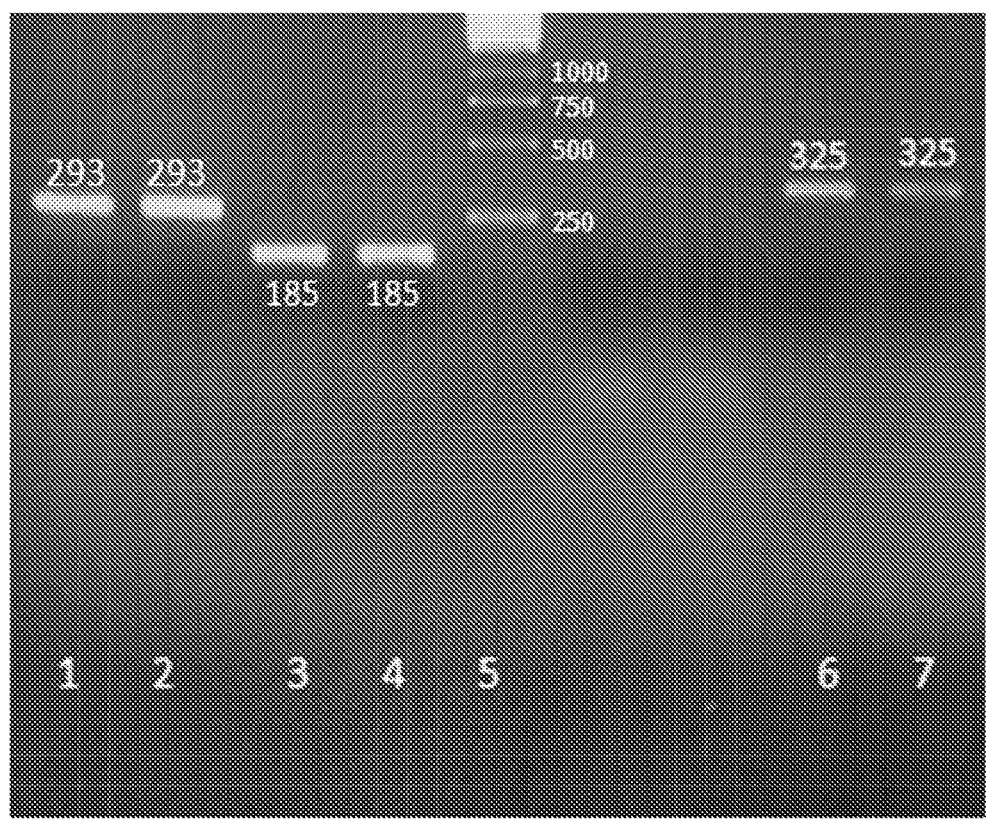
FIG. 8 illustrates the results Of RT-PCR on RNA samples and expression analysis of ILV5 in the presence and absence of the synthesized antifungal drug, according to one embodiment herein.

FIG. 8 illustrates the expression analysis of ILV5 in the presence and absence of the synthesized antifungal drug, according to the embodiments herein. RNA samples were prepared after 4 hours of treating yeast cells with drug compound. With respect to FIG. 8, the results Of RT-PCR on RNA samples and expression analysis of ILV5 in the presence and absence of the synthesized antifungal drug. The result of RT-PCR on RNA samples from drug treated and untreated samples can be seen. Actin was used as a loading control in RT-PCR experiments. The Lane 1 and Lane 2 show the bands for PCR products amplified with actin primers in treated and untreated samples. The Lane 3 and Lane 4 show the bands for PCR products amplified with ilv2 primers in treated and untreated samples. The Lane 6 and Lane 7 show bands for PCR products amplified with ilv5 primers in treated and untreated samples at 325 bp. The Lane 5 represents the DNA size marker. As it can be inferred and confirmed from FIG. 8 that the Expression level of ilv5 in the treated cells are higher than that in the untreated cells. The expression levels of ilv2 and ilv3 were unchanged.

in Silico Study of the Cell Target Molecule and the Antifungal Compound:

The mode of connection between antifungal synthetic compound and ILV5 enzyme i.e. Acetohydroxyacid reductoisomerase was studied through in silico docking experiment by Arguslab software. The study supported in the in vitro experimental findings. The target protein was used as a receptor for the compound B according to the embodiments herein. In addition, a set of other compounds were also used to compare the result. The interaction energy of compound B with the target protein or enzyme is quite low and showed a potent affinity for that protein.

The Investigation of an interaction between the compounds and the target enzyme was carried out by the ArgusLab application. The interaction energy level was −8.25921 Kcal/mol.

Figure 9:
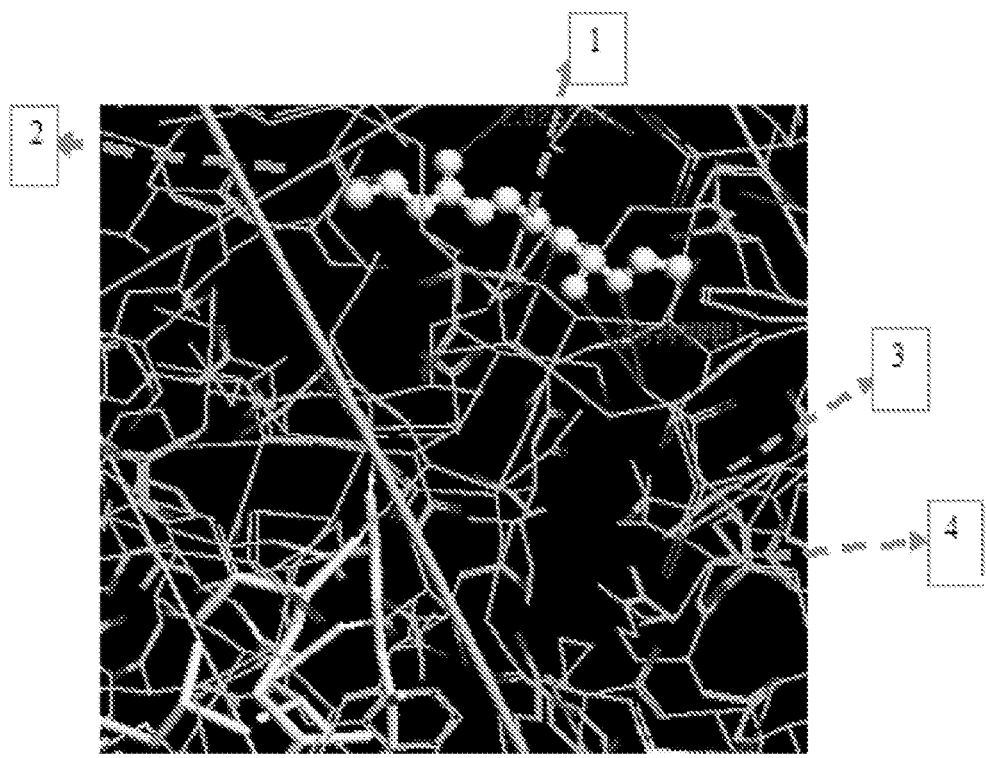
FIG. 9 shows a molecular model illustrating a mode of connection between antifungal synthesized compound and ilv5 enzyme (Acetohydroxy acid reductoisomerase), according to the embodiment herein.

FIG. 9 shows a molecular model illustrating a mode of connection between antifungal synthesized compound and ilv5 enzyme (Acetohydroxy acid reductoisomerase), according to the embodiment herein. A molecular model indicates the mode of connection between antifungal synthesized compound and ilv5 enzyme i.e. Acetohydroxy acid reductoisomerase taken by ArgusLab software, according to the embodiment herein. With respect to FIG. 9, the point (1) which is Yellow in color shows the antifungal compound. The point (2) representing yellow residues are the amino acids of an active site. The green line is the docking box. The point (3) in Red color is the oxygen molecule. The point (4) which is in grey color is the carbon skeleton. As seen in FIG. 9, the antifungal compound synthesized according to the embodiments herein has a good interaction with the enzyme in its dock position. Other molecules with varying structures were examined in the same in silico condition. The compound B showed the low interaction energy and high absolute value. The compound B showed a suitable position in the dock experiment confirming the other observed results indicated in the study.

The embodiments herein provide new antifungal compounds that work by inhibiting the synthesis of aliphatic amino acids in the fungal biological systems and thus do not lead to resistance. The mode of action of new antifungal compounds is determined through the reversal assay technique. The inhibitory effect of the antifungal compound is reversed by adding the different concentrations of various metabolic intermediates or building block molecules. In this way the inhibited metabolic pathway is recognized. The mechanism of synthesis of antifungal compounds is provided. Indeed the pathway through which the drug is inhibited is defined by the reversal assay. In other word, the effect of synthesized compounds on the biosynthesis of amino acids, nucleic acids and citric acid cycle is studied.

The application of reversal assay method for identification and a development of the new derivatives having anti-fungal activity is not seen before. Further the experimental design and patterned usage of the metabolites as a systematic way of pin pointing the pathway that contains the possible inhibition spots is also new.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. An aliphatic amino acid biosynthesis inhibitor composition having an antifungal activity, the composition comprising:
   a compound A, wherein the compound A is 2-oxo-2H-chromen-7-yl propiolate and wherein the compound 2-oxo-2H-chromen-7-yl propiolate is shown by a formula (1)

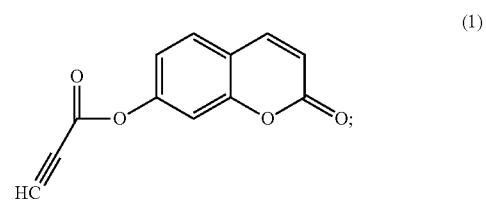 [SMILES: C#CC(=O)Oc1ccc2ccc(=O)oc2c1]

a compound B, wherein the compound B is diethyl-hex-2-en-4-yne-dioate and wherein the compound diethyl-hex-2-en-4-yne-dioate is shown by formula (2)

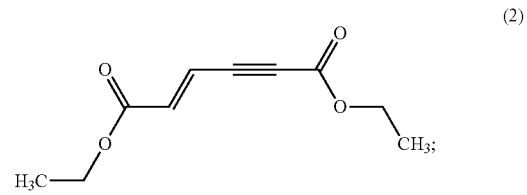

a compound C, wherein the compound C is dinonyl-hex-2-en-4-yne-dioate and wherein the compound dinonyl-hex-2-en-4-yne-dioate is shown by formula (3)

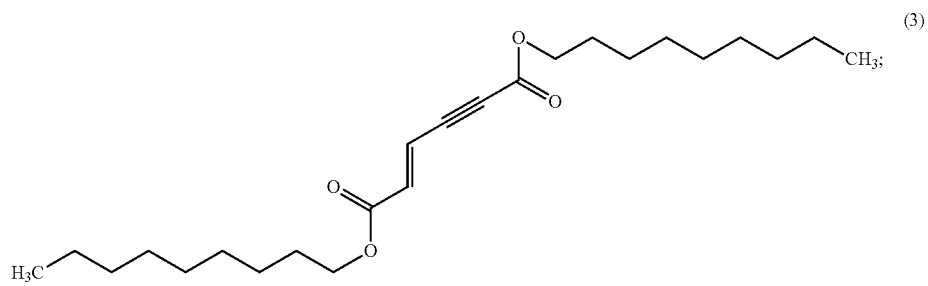 [SMILES: CCCCCCCCCOC(=O)C#C/C=C/C(=O)OCCCCCCCCC]

and
a compound D, wherein the compound D is shown by formula (4)

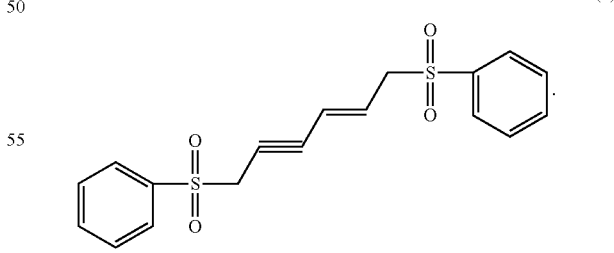

2. The composition according to claim 1, wherein the composition inhibits a biosynthesis of an aliphatic amino acid in a fungal biological system and wherein the aliphatic amino acid is selected from a group consisting of leucine, isoleucine and valine.

3. The composition according to claim 1, wherein the composition is used with a concentration of 0-200 µg/ml.

4. A method of synthesizing an aliphatic amino acid biosynthesis inhibitor composition having an antifungal activity comprising the steps of:
preparing a solution A, wherein the solution A is prepared by mixing a compound E and a compound F, wherein the compound E is dicyclohexylcarbodiimide (DCC) and the compound F is Dimethylaminopyridine (DMAP);
preparing a solution B, wherein the solution B is prepared by mixing a compound containing a hydroxyl group, an acetylene carboxylic acid and a solvent;
adding a prepared solution A to a prepared solution B to obtain a first mixture, wherein the prepared solution A is added to the prepared solution B at a predetermined temperature range drop wise over a predetermined time period, wherein the predetermined temperature range is 0° C.-4° C., wherein the predetermined time period is 1 hr;
stirring the obtained first mixture for a predetermined time to obtain a residue, wherein the predetermined time is 5 hrs;
dissolving the residue in the solvent at a predefined temperature to obtain a second mixture, wherein the predefined temperature is 0° C.;
stirring the second mixture with a catalyst for a predefined time, wherein the predefined time is 30 minutes; and
evaporating a stirred second mixture to obtain a compound, wherein the compound is hex-2-en-4-yn-1,6-dioate derivative compound.

5. The method according to claim 4, wherein the compound containing the hydroxyl group includes 7-hydroxy-chromen-2-one, ethanol and nonane-1-ol.

6. The method according to claim 4, wherein the acetylene carboxylic acid is propiolic acid.

7. The method according to claim 4, wherein the solvent is dichloromethane.

8. The method according to claim 4, wherein the residue includes 2-oxo-2H-chromen-7-yl propiolate, ethyl propiolate, dodecyl propiolate and (Ethynylsulfonyl)benzene.

9. The method according to claim 4, wherein the catalyst includes N,N'-Dicyclohexylcarbodiimide (DCC), 4-Dimethylaminopyridine (DMAP), and 1,4-diazabicyclo[2.2.2]octane (DABCO).

10. The method according to claim 4, wherein the composition includes a compound A, a compound B, a compound C and a compound D, and wherein the compound A is 2-oxo-2H-chromen-7-yl propiolate and wherein the compound 2-oxo-2H-chromen-7-yl propiolate is shown by formula (1)

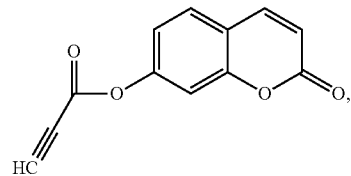

wherein the compound B is diethyl-hex-2-en-4-yne-dioate and wherein the compound diethyl-hex-2-en-4-yne-dioate is shown by formula (2)

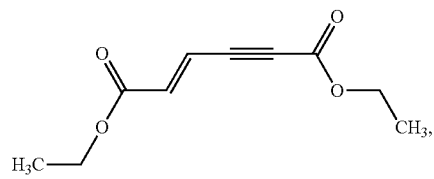

wherein the compound C is dinonyl-hex-2-en-4-yne-dioate and wherein the compound dinonyl-hex-2-en-4-yne-dioate is shown by formula (3)

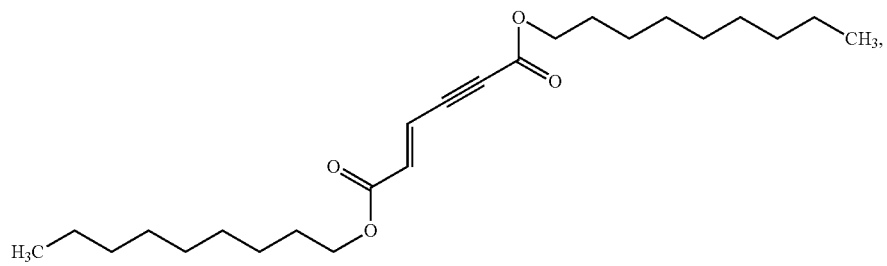

and
wherein the compound D is shown by formula (4)

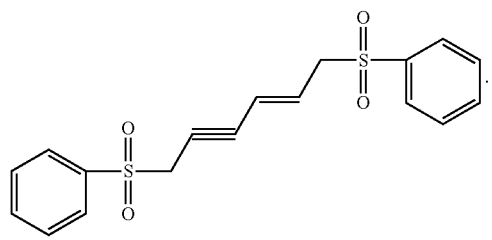

11. The method according to claim 4, wherein the composition inhibits a biosynthesis of an aliphatic amino acid in a fungal biological system, wherein the amino acid is selected from a group consisting of leucine, isoleucine and valine.

12. The compound according to claim 4, wherein the composition is used with a concentration of 0-200 µg/ml.

* * * * *